United States Patent [19]
Tan

[11] Patent Number: 5,193,404
[45] Date of Patent: * Mar. 16, 1993

[54] LIQUIDS SAMPLER

[75] Inventor: Samantha S. H. Tan, Fremont, Calif.

[73] Assignee: Balazs Analytical Laboratory, Sunnyvale, Calif.

[*] Notice: The portion of the term of this patent subsequent to Jun. 5, 2007 has been disclaimed.

[21] Appl. No.: 654,316

[22] Filed: Feb. 12, 1991

[51] Int. Cl.$^5$ .............................................. G01N 1/20
[52] U.S. Cl. ................................................. 73/864.34
[58] Field of Search ........... 73/863.81, 863.83, 863.84, 73/864.34, 864.35, 864.51, 864.63, 864.34; 137/147-149, 205; 141/27, 59, 60; 417/118, 148

[56] References Cited

U.S. PATENT DOCUMENTS

| | | | |
|---|---|---|---|
| 3,062,056 | 11/1962 | Wicoff | 73/864.34 |
| 4,548,088 | 10/1985 | Hood, Jr. | 73/864.34 |
| 4,612,815 | 9/1986 | Green et al. | 73/864.51 |
| 4,930,360 | 6/1990 | Tan | 73/864.34 |

FOREIGN PATENT DOCUMENTS

| | | | |
|---|---|---|---|
| 2632727 | 12/1989 | France | 73/864.34 |
| 859855 | 8/1981 | U.S.S.R. | 73/864.34 |

Primary Examiner—Robert Raevis
Attorney, Agent, or Firm—Fliesler, Dubb, Meyer & Lovejoy

[57] ABSTRACT

An apparatus is set forth for removing a sample of a liquid for chemical analysis from a vessel containing the liquid and for delivering the sample into a sample bottle. The apparatus comprises a hollow member defining an enclosed plenum. A sample bottle attachment structure defines a passage communicating with the plenum and being adapted for attachment to a top portion of the sample bottle. A first partition structure blocks off the passage other than where it communicates with the plenum. A longitudinally extending sample transport tube extends through the passage and into the bottle. The transport tube passes through the first partition in substantially air-tight relation to it. The other end of the transport tube is positionable in the liquid being sampled.

4 Claims, 2 Drawing Sheets

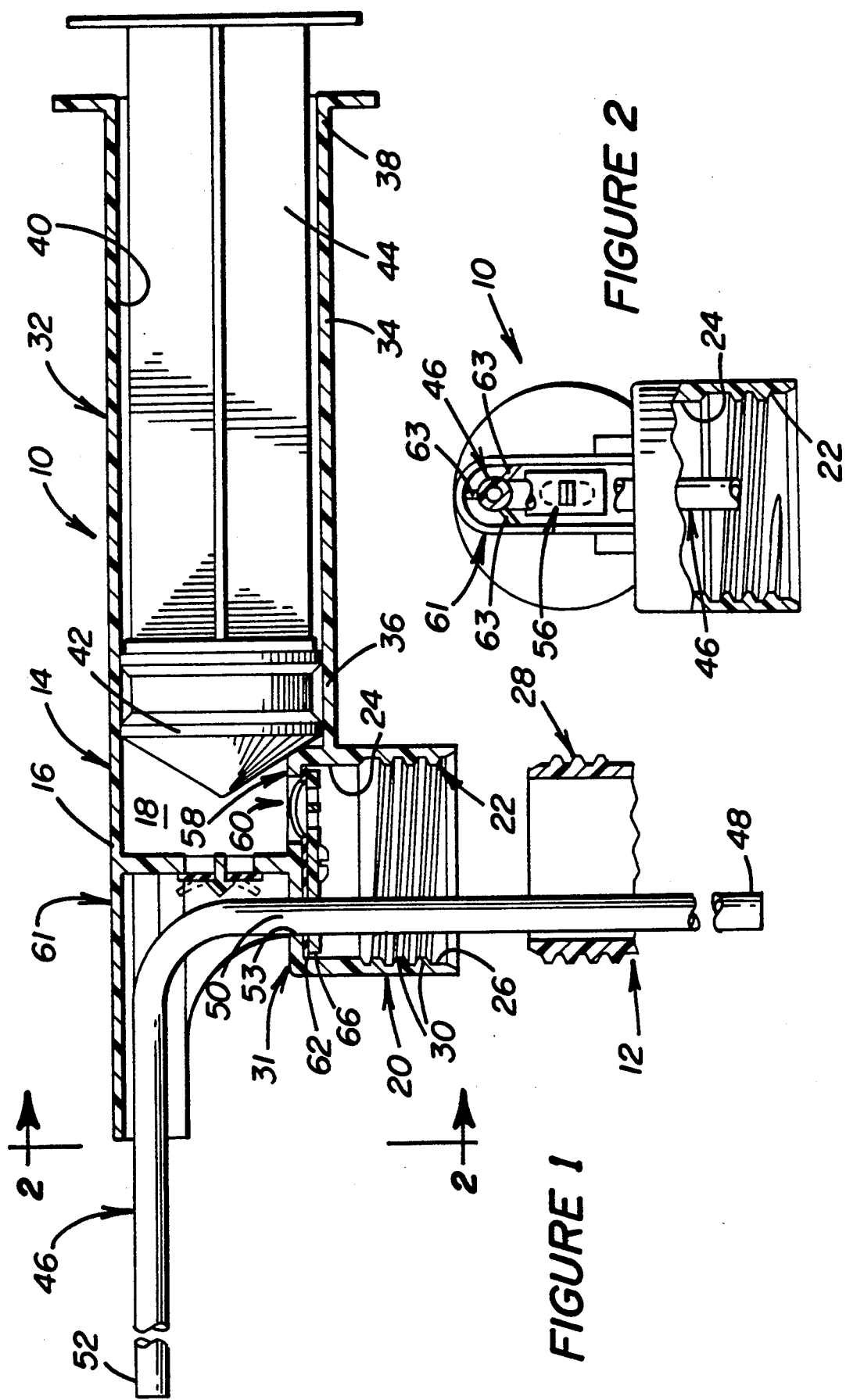

LIQUIDS SAMPLER

DESCRIPTION

1. Technical Field

The present invention relates to a device or apparatus for obtaining a non-contaminated sample of a liquid suitable for chemical analysis. The invention further relates to a method for carrying out such sampling.

2. Background of the Invention

Numerous industries utilize liquid chemicals and are faced with the problem of being able to analyze the chemicals they have on hand, or are using in a process, to ensure that they have not become contaminated or otherwise unsuitable for use. Such chemicals may be, for example, water, organic liquids, acids, bases or ammonia. There is, for example, a very serious problem in the semiconductor processing industry wherein small amounts of impurities in ultra pure water being utilized to, for example, process silicon wafers, can lead to the production of unsatisfactory product which cannot be sold. The purity of water in nuclear reactor cooling systems must also be regularly and accurately determined, thus requiring non-contaminating sampling. Further, environmental concerns require that waste liquids be analyzed prior to disposal.

In the past, such samples as have been discussed above have been removed in a number of ways. For example, they have been removed by utilizing taps from which some of the liquid can be run off into sample bottles, by utilizing pipettes, by pouring and by ladling. One problem with these methods is that contamination can occur during the sampling procedure. Another serious problem with these methods is that of assuring that the sample taken is truly representative of the liquid being sampled. For example, if one utilizes a tap, then the sample is that which is adjacent the tap and not necessarily representative of the bulk composition of the liquid. The same can happen if one pours a sample out of the liquid into a sample bottle. If one utilizes a ladle, there is an open sample being transferred which can be contaminated during the transfer process. A pipette, if properly cleaned, does not have these problems, but there is still the extra required step of transferring from the pipette into a sample bottle which is then sent off to a laboratory for analysis. Thus, there is an extra step during which contamination can occur.

The present invention is directed to overcoming one or more of the problems as set forth above.

DISCLOSURE OF THE INVENTION

In accordance with an embodiment of the present invention, an apparatus is set forth for removing a sample of a liquid for chemical analysis from a vessel containing the liquid and for delivering the sample into a sample bottle. The apparatus comprises a hollow member defining an enclosed plenum. A sample bottle attachment structure defines a passage communicating with the plenum and being adapted for attachment to a top portion of the sample bottle. A first partition structure blocks off the passage other than where it communicates with the plenum. A longitudinally extending sample transport tube extends through the passage and into the bottle. The transport tube passes through the first partition in substantially air-tight relation to it. The other end of the transport tube is positionable in the liquid being sampled.

In accordance with another embodiment of the present invention, an apparatus is set forth for removing a sample of a liquid for chemical analysis from a vessel containing the liquid and for delivering the sample into a sample bottle. The apparatus comprises a hollow member having a wall structure defining an enclosed plenum. A barrel has a first end portion and a second end portion and defines a bore with the first end portion being in flow communication with the plenum. A piston is slidably reciprocally positioned in close-fitting relation in the bore. A piston motivating member extends into the bore from the second end portion and is attached to the piston. A sample bottle attachment structure defines a passage having a first end portion communicating with the plenum and a second end portion adapted for attachment to a top portion of the sample bottle. A first partition structure blocks off the passage other than where it communicates with the plenum. A longitudinally extending sample transport tube has a first end portion which extends through the passage into the bottle. The transport tube passes through the first partition structure in substantially air-tight relation to it. A second end portion of the tube is adapted for positioning in the liquid being sampled.

The present invention allows the placement of one end of a sample transport tube into a position in a liquid to be sampled whereat a fully representative sample of the liquid can be drawn. There is no contamination possible between the liquid being sampled and the sample bottle which receives that liquid. The particular structure utilized provides support which properly positions the proximal end of the sampling tube in the sample receiving bottle. Thus, one can obtain and preserve the integrity of a representative liquid sample for analysis.

BRIEF DESCRIPTION OF THE DRAWINGS

The invention will be better understood by reference to figures of the drawings wherein like numbers denote like parts throughout and wherein:

FIG. 1 illustrates, in side sectional partial view, an apparatus in accordance with an embodiment of the present invention;

FIG. 2 illustrates, in partially cut away front end view, a portion of the apparatus shown in FIG. 1;

BEST MODE FOR CARRYING OUT INVENTION

Figure 5:
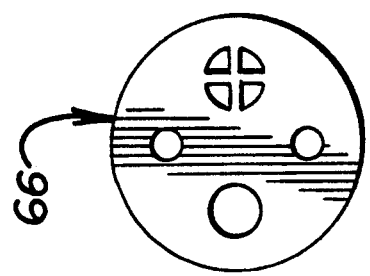
FIGS. 4 and 5 illustrate, in bottom views, the gasket and gasket retainer which form portions of the valving structure also illustrated in FIG. 3.

In accordance with an embodiment of the present invention, an apparatus 10 is utilized for removing a sample of a liquid for chemical analysis from a vessel (not shown) containing the liquid and for delivering the sample into a sample bottle 12. The sample bottle 12 can be of the screw-cap variety whereby a cap (not shown) can be screwed onto the sample bottle 2 to preserve the integrity of the sample once the sample has been transferred into the sample bottle 12. Alternatively, the sample bottle 12 can be such as to provide a snap-in compression fit. The size of the sample bottle 12 can be selected by the person doing the sampling so as to provide the desired sample size.

Referring principally to FIG. 1, a hollow member 14 has a wall structure 16 defining an enclosed plenum 18.

A sample bottle attachment structure 20 defines a passage 22 having a first end portion 24 communicating with the plenum 18 and a second end portion 26 adapted for attachment to a top portion 28 of the sample bottle 12. The sample bottle attachment structure 20 can include screw threads 30 to accomplish this attachment.

Figure 3:
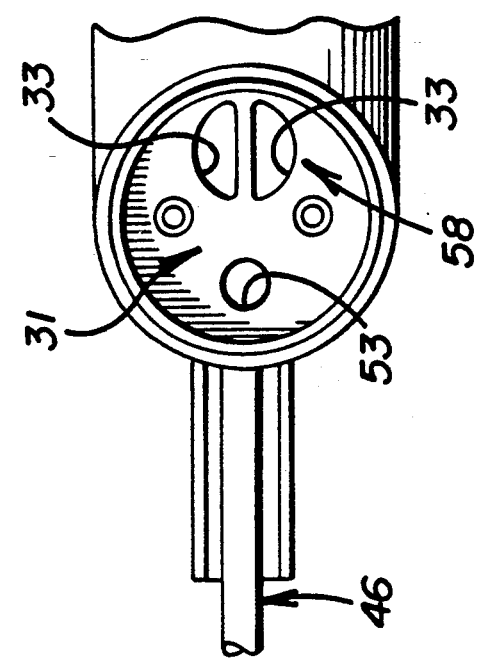
FIGS. 3 illustrates, in partial bottom view, a detail in the partition and valving structure of the embodiment of FIG. 1.

The passage 22, in the embodiment illustrated the first end portion 24 thereof, is blocked off by a first partition 31 other than where the passage 22 communicates with the plenum 18 via openings 33 (FIG. 3).

Hand-pumping means 32, suitably of a nature which will be described in following, are used for manually creating a partial vacuum in the plenum 18 and thereby also providing a partial vacuum, via the sample bottle attachment structure 20, in the sample bottle 12. In accordance with the embodiment as illustrated in the Figures, and as is preferred for reasons of economy, the sample bottle attachment 20 is made integrally with the hollow member 14.

In the embodiment illustrated, the hand-pumping means 32 comprises a barrel 34 having a first end portion 36 and a second end portion 38 and defining a bore 40. The first end portion 36 is in flow communication with the plenum 18. A piston 42 is slidably reciprocally positioned in close-fitting relation in the bore 40. A piston motivating member 44 extends into the bore 40 from the second end portion 38 thereof and is attached to and serves to motivate the piston 42. The piston motivating member 44 can be integral with the piston 42. However, generally the piston 42 and the piston motivating member 44 will be formulated of different materials. For example, the piston 42 can be an elastomeric material while the piston motivating member 44 can be of a more rigid plastic construction. Basically the barrel 34, the piston 42 and the piston motivating member 44 are like those used in a common hypodermic syringe, although the size can be selected, as desired, so as to remove as large a sample as desired. Volume indicia can be provided on the barrel 34, if desired, to indicate the volume being drawn.

A longitudinally extending sample transport tube 46 has a first end portion 48, a central portion 50 and a second end portion 52. The first end portion 48 of the transport tube 46 extends through the passage 22 and through the top portion 28 of the sample bottle 12. It suitably terminates above a bottom portion (not shown) of the bottle 12 and below the top portion 28 of the bottle 12. It is preferable that the first end portion 48 of the transport tube 46 terminate above the sample level in the sample bottle 12 to prevent possible contamination of the sample through contact with the exterior of the transport tube 46. The central portion 50 of the transport tube 46 passes through the first partition structure 31 in substantially air-tight relation to it as shown at 53 in FIGS. 1 and 3. It should be recognized that it is not necessary that the transport tube 46 be in completely air-tight relation to the wall structure 16. All that is needed is a reasonably tight fit so that the liquid can be drawn into the sample bottle 12 before the vacuum is lost due to leakage where the tube 46 passes through the first partition structure 31. Indeed, it may be desirable to replace one transport tube 46 with another to avoid contamination. In such an instance, it is necessary that one be able to remove the old tube 46 and to feed another through the first partition structure 31 into its place. The second end portion 52 of the transport tube 46 is adapted for positioning in the liquid in the vessel being sampled.

The first end portion 48 of the transport tube 46 is suitably held in position by the first partition structure 31 which holds the central portion 50 of the transport tube 46. A second partition structure 58 blocks communication of the plenum 18 with the passage 22 if a valve 60 is present as discussed below. If the valve 60 is not present one or more holes must be present in the second partition structure 58 to allow evacuation of the sample bottle 12. Generally, the first partition structure 31 and the second partition structure 58 will be integrally formed.

A first valve 56 may be present which communicates with the plenum 18, the first valve 56 being adapted to allow flow of air through it from the plenum 18 to the surrounding atmosphere and to prevent flow of air through the valve 56 from the surrounding atmosphere into the plenum. The reason for including the first valve 56 is that it may be desirable to make several strokes of the piston 42 in order to obtain sufficient liquid sample in the sample bottle 12. During the forward stroke of the piston 42, that is when it is being pushed into the barrel 34 towards the hollow member 14, air can flow out of the first valve 56. Then, when the piston 42 is pulled through the barrel 34 away from the hollow member 14, the first valve 56 is closed whereby the necessary partial vacuum is created within the plenum 18 and within the sample bottle 12. Once one stroke worth of liquid has been collected in the sample bottle 12, this procedure can be repeated as many times as desired to obtain the desired amount of liquid sample. It should be noted that the apparatus 10 will operate and is useful even if the valve 56 is omitted.

It may be advantageous in certain instances to include the second partition structure 58 for blocking communication of the plenum 18 with the passage 22 along with the second valve 60 which communicates the plenum 18 with the passage 22, the second valve 60 being adapted to allow flow of air therethrough from the passage 22 into the plenum 18 when the pressure in the passage 22 exceeds that in the plenum 18 by at least a selected amount. When the piston 42 is moved forward the second valve 60 prevents air from entering the sample bottle 12 thus preserving the integrity of any sample portion previously collected. When a vacuum is created in the plenum 18 by use of the hand-pumping means 32, the pressure differential is significantly overcome whereby a vacuum can be created in the sample bottle 12 which is only slightly less than that in the plenum 18. When the piston 42 is advanced the valve 60 also prevents air from being pumped into the bottle 12 and via the tube 46 back into the vessel being sampled. The second partition structure 58 along with the second valve 60 can be utilized by themselves (in which case only a single withdrawing stroke of the piston 42 can be utilized) or in combination with the first valve 56 thereby allowing multi-stroke operation of the piston 42. It should be noted that the partition 58 (and, of course the second valve 60) is not necessary to operation of the apparatus 10, i.e., the second partition structure 58 can simply be omitted, in which case only a single withdrawing stroke of the piston 42 can be utilized unless the quantity of liquid sampled into the sample bottle 12 has a liquid level below the first end portion 48 of the transport tube 46 or other means are provided for expressing air form the plenum 18 without expelling liquid from the sample bottle 12.

A hood structure 61 can extend forwardly from the barrel 34 for protection of the integrity of the tube 46 and of the first valve 56, when present. The hood structure 61 can include a rib structure 63 for supporting the tube 46.

Figure 4:
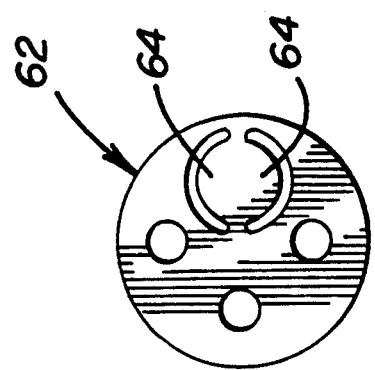

FIGS. 3, 4 and 5 illustrate a suitable valve 60. The valve illustrated is a check valve comprising a flexible gasket 62 having a pair of flaps 64 which can block the openings 33. A retainer gasket 66 holds the flexible gasket 62 in position and has openings 68 through which air can flow when the piston 44 is retracted. Other types of check valves can also be used.

As will be noted, the embodiments illustrated show the transport tube 46 proceeding upwardly through the passage 22 and then through the first partition structure 31 and finally exiting at a right angle to the alignment of the sample bottle 12. It has been found that this arrangement is advantageous in that the transfer tube 46 comes out at a good angle for inserting its second end portion 52 into the liquid to be sampled.

In operation, the first end portion 48 of the transfer tube 46 is positioned in the sample bottle 12. The second end portion 52 of the transport tube 46 is inserted into the liquid being sampled. A hand-operated pump, that is the hand-pumping means 32, is utilized to manually create a partial vacuum in the sample bottle 12 of sufficient magnitude to draw the liquid sample through the transfer tube 46 and into the sample bottle 12. In accordance with the embodiment of the invention illustrated and preferred, the hand-operated pump is utilized by moving the piston 42 in the barrel 34 to create the partial vacuum at the end 36 of the barrel 34 away from which the piston 42 is moved and the end 36 of the barrel 34 having the partial vacuum is communicated with the interior of the sample bottle 12 at a position above the entrance to the second end portion 52 of the transport tube 46. Industrial Applicability The present invention provides the capability for obtaining a sample of a liquid which is representative of its bulk composition. The chances of contamination of the sample are minimized. Furthermore, the sampling can be carried out readily and quickly even by someone not highly trained in the analytical chemistry art. Further, in accordance with an embodiment of the invention, the amount of sample taken can be varied dependent upon the amount of sample wanted in sample bottle 12.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. An apparatus for removing a sample of a liquid for chemical analysis from a vessel containing said liquid and for delivering said sample into a sample bottle, comprising:
   a hollow member having a wall structure partially defining an enclosed plenum;
   a sample bottle attachment structure defining a passage having a first end portion communicating with said plenum and a second end portion adapted for attachment to a top portion of said sample bottle;
   a first partition structure partially defining said plenum and blocking off said passage other than where said first end portion communicates with said plenum;
   hand pumping means for manually creating a partial vacuum in said plenum;
   a longitudinally extending sample transport tube having a first end portion, a central portion and a second end portion, said first end portion of said tube extending through said passage into said bottle, said central portion passing through said first partition structure in substantially air tight relation thereto and said second end portion of said tube being adapted for positioning in said liquid in said vessel, said first partition structure holding said central portion of said transport tube and thereby supporting said first portion of said sample tube in said bottle; and
   a first valve communicating with said plenum, said valve being adapted to allow flow of air therethrough from said plenum to a surrounding atmosphere and to prevent flow of air therethrough from the surrounding atmosphere into said plenum;
   and wherein said communicating of said first end portion of said passage with said plenum is provided by a construction comprising:
   a second partition structure blocking communication of said plenum with said passage other than via one or more openings through said second partition structure; and
   a second valve communicating said plenum with said passage, said second valve being adapted to allow flow therethrough from said passage and through said one or more openings into said plenum only if the pressure in said passage exceeds that in said plenum by at least a selected amount.

2. An apparatus as set forth in claim 1, wherein said first and second partition structures are part of a single partition.

3. An apparatus for removing a sample of a liquid for chemical analysis from a vessel containing said liquid and for delivering said sample into a sample bottle, comprising:
   a hollow member having a wall structure partially defining an enclosed plenum;
   a sample bottle attachment structure defining a passage having a first end portion communicating with said plenum and a second end portion adapted for attachment to a top portion of said sample bottle;
   a first partition structure partially defining said plenum and blocking off said passage other than where said first end portion communicates with said plenum;
   a barrel having a first end portion and a second end portion and defining a bore therealong, said first end portion being in flow communication with said plenum;
   a piston slidably reciprocally positioned in close fitting relation in said bore;
   a piston motivating member extending into said bore from said second end portion thereof and being attached to said piston;
   a longitudinally extending sample transport tube having a first end portion, a central portion and a second end portion, said first end portion of said tube extending through said passage into said bottle, said central portion passing through said first partition structure in substantially air tight relation thereto and said second end portion of said tube being adapted for positioning in said liquid in said vessel, said first partition structure holding said central portion of said transport tube and thereby positioning said first end portion of said transport tube in said bottle;

a first valve communicating with said plenum, said valve being adapted to allow flow of air therethrough from said plenum to a surrounding atmosphere and to prevent flow of air therethrough from the surrounding atmosphere into said plenum: and wherein said communicating of said first end portion of said passage with said plenum is provided by a construction comprising:

a second partition structure blocking communication of said plenum with said passage other than via one or more openings through said second partition structure; and a second valve communicating said plenum with said passage, said second valve being adapted to allow flow of air therethrough from said passage and through said one or more openings into said plenum only if the pressure in said passage exceeds that in said plenum by at least a selected amount.

4. An apparatus as set forth in claim 3, wherein said first and second partition structures are part of a single partition.

* * * * *